(12) United States Patent
Franks

(10) Patent No.: US 9,566,385 B2
(45) Date of Patent: Feb. 14, 2017

(54) INTRAVENOUS PISTON PUMP DISPOSABLE AND MECHANISM

(71) Applicant: CareFusion 303, Inc., San Diego, CA (US)

(72) Inventor: Brett H. Franks, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 14/249,266

(22) Filed: Apr. 9, 2014

(65) Prior Publication Data

US 2014/0221973 A1    Aug. 7, 2014

Related U.S. Application Data

(62) Division of application No. 12/472,710, filed on May 27, 2009, now Pat. No. 8,733,736.

(30) Foreign Application Priority Data

May 26, 2010  (WO) .................. PCT/US2010/03623

(51) Int. Cl.
*A61M 5/168* (2006.01)
*A61M 5/142* (2006.01)
(Continued)

(52) U.S. Cl.
CPC ....... *A61M 5/16881* (2013.01); *A61M 5/1422* (2013.01); *A61M 5/14216* (2013.01);
(Continued)

(58) Field of Classification Search
CPC .. A61M 5/1422; A61M 5/16881; A61M 5/36; A61M 39/223; A61M 2039/224; A61M 2039/229; A61M 2005/1402; A61M 2005/1403; A61M 2205/128; A61M 2206/22; F04B 1/063; F04B 27/0673; F16K 11/08–11/0876
(Continued)

(56) References Cited

U.S. PATENT DOCUMENTS 4,382,753 A * 5/1983 Archibald ......... A61M 5/14224
  417/479
4,534,758 A * 8/1985 Akers ................. A61M 5/1409
  604/247
(Continued)

FOREIGN PATENT DOCUMENTS

JP   H024381 A    1/1990
JP   2005508712 A 4/2005

OTHER PUBLICATIONS

Korean Office Action for Application No. 10-2011-7027665, dated Aug. 5, 2016, 7 pages excluding English translation.

*Primary Examiner* — Laura Bouchelle
*Assistant Examiner* — Anh Bui
(74) *Attorney, Agent, or Firm* — McDermott Will & Emery LLP

(57) ABSTRACT

An apparatus for delivery of fluids to a patient includes an inlet tube and an outlet tube connected to each other at an angular joint. A rotary valve and a piston are fitted to the angular joint forming a chamber. The rotary valve is provided with a priming channel notch and a pumping notch. For priming operation with the fluid delivery apparatus, a user sets the rotary valve to a priming position. During pumping operation, the rotary valve rotates in coordination with the piston to transfer a quantum of fluid from the inlet tube to the outlet tube via the chamber. A second piston is optionally provided on the outlet tube for smoothing out flow rate pulsations.

20 Claims, 20 Drawing Sheets

(51) Int. Cl.
    *A61M 5/36*     (2006.01)
    *F04B 1/06*     (2006.01)
    *F04B 27/067*     (2006.01)
    *F16K 5/04*     (2006.01)
    *F16K 11/085*     (2006.01)
    *A61M 39/22*     (2006.01)
    *A61M 5/14*     (2006.01)

(52) U.S. Cl.
    CPC ............ *A61M 5/36* (2013.01); *A61M 39/223* (2013.01); *F04B 1/063* (2013.01); *F04B 27/0673* (2013.01); *F16K 5/0407* (2013.01); *F16K 11/085* (2013.01); *A61M 2005/1402* (2013.01); *A61M 2005/1403* (2013.01); *A61M 2039/224* (2013.01); *A61M 2039/229* (2013.01); *A61M 2205/128* (2013.01); *A61M 2206/22* (2013.01)

(58) Field of Classification Search
    USPC ........................................ 137/625.21, 625.22
    See application file for complete search history.

(56) References Cited

U.S. PATENT DOCUMENTS

| | | | |
|---|---|---|---|
| 4,605,396 A | 8/1986 | Tseo et al. | |
| 4,850,980 A | 7/1989 | Lentz et al. | |
| 4,904,245 A * | 2/1990 | Chen | A61M 3/0233 137/625.47 |
| 5,971,912 A | 10/1999 | Honma et al. | |
| 6,500,156 B1 | 12/2002 | Stansbury | |
| 7,462,170 B2 | 12/2008 | Fournie et al. | |
| 2003/0127098 A1* | 7/2003 | Fjeld | A61M 16/20 128/204.26 |
| 2008/0287872 A1* | 11/2008 | Patzer | 604/131 |
| 2009/0264720 A1* | 10/2009 | Torjman | A61B 5/1411 600/322 |
| 2010/0204645 A1* | 8/2010 | Dorsey | A61M 39/223 604/65 |

\* cited by examiner

INTRAVENOUS PISTON PUMP DISPOSABLE AND MECHANISM

CROSS-REFERENCES TO RELATED APPLICATIONS

This application is a Divisional of U.S. application Ser. No. 12/472,710 entitled "Intravenous Piston Pump Disposable & Mechanism," filed May 27, 2009, and is a Continuation Application of, and claims priority to PCT Application No. PCT/US2010/036230 entitled "Intravenous Piston Pump Disposable & Mechanism," filed May 26, 2010, designating the United States of America, which are hereby incorporated by reference in their entirety.

FIELD

The present disclosure relates, in general, to a medical fluid delivery system, and more particularly, to a medical fluid delivery system with a rotary valve.

BACKGROUND

Delivery of fluids to and from a patient's body is often part of a medical treatment. A variety of mechanized fluid delivery system designs have been used. Generally speaking, these designs combine a valve mechanism to sequester the flow in one direction and a pump mechanism to deliver the flow in that direction. Most designs either use a push valve to push against a membrane and sequester the flow by occluding flow in one direction and then pump mechanism to displace a desired amount of fluid or use a rotary valve to sequester flow by a "scoop" while occlude flow in one direction and then using the pumping mechanism to deliver a desired amount of fluid. The desired amount of fluid is then provided to the patient.

In a typical push valve type system, fluid occlusion is achieved by advantageously employing the elastic property of a membrane. In practice, a push valve type system suffers from certain drawbacks. The fluid delivery mechanism of occlusion by pressing on a membrane forces the volume beneath the membrane to be delivered to both sides of the occlusion path. The fluid delivery mechanism's reliance on the elasticity property results in imprecise volumetric delivery of fluids. Furthermore, the volume dispensed through the system may be sensitive to the elevation of the pump, the fluid reservoir and the patient with respect to each other. The flow rate in a push valve type fluid delivery system may vary by as much as 20% based on the configuration of the reservoir and the patient.

In a typical rotary valve system, such as disclosed in the U.S. Pat. No. 4,605,396, a valve is rotated to alternately provide fluid communication through a groove between an inlet and a pump chamber or between the pump chamber and an outlet.

In practice, a rotary valve system has certain shortcomings. For example, priming such a system to expel air out of the fluid channels requires wasting some fluid by turning on the rotary valve and letting some fluid escape the delivery system to ensure air is removed from the system.

SUMMARY

There is a need for a fluid delivery system that maintains high flow rate accuracy regardless of positioning of the system with respect to a fluid reservoir and a patient, and can be easily primed without suffering from fluid drawback.

This and other needs are met by embodiments of the present disclosure that have a rotary valve fluid delivery system that provides easy priming and minimizes fluid loss during priming.

This and other needs are met by embodiments of the present disclosure that have a valve apparatus that can deliver fluid by rotating in one direction (either clockwise or counterclockwise), advantageously using a configuration in which priming takes place on the underside of the valve along a separate pathway from delivery of fluid.

In a first exemplary aspect, a fluid delivery apparatus is disclosed comprising an inlet tube having a channel for passage of fluid from a proximal end to a distal end, an outlet tube having a channel for passage of fluid from a proximal end to a distal end, an angular joint formed by a connection between the distal ends of the inlet tube and the outlet tube, the angular joint having an internal cavity connected between the channels of the inlet tube and the outlet tube, a first piston configured to reciprocate in a first enclosure fluidly connected to the internal cavity, the first piston having a first aspiration cavity with a first aspiration capacity; and a valve rotatably positioned within the internal cavity, the valve configured to fluidly couple the inlet tube and the outlet tube in a priming position of the valve and to convey fluid between the inlet tube and the outlet tube and from the first aspiration cavity when the valve is rotated between a first pumping position and a second pumping position.

In a second exemplary aspect, a method of delivering fluid from an inlet tube connected to a fluid reservoir to an outlet tube in a pumping cycle, comprising positioning, during an inflow phase of the pumping cycle, a valve to a first pumping position to establish a fluid contact between the inlet tube and a first aspiration cavity without having a fluid connection between the first aspiration cavity and the outlet tube, moving, during the inflow phase, a first piston connected to the first aspiration cavity to increase the volume of the first aspiration cavity, positioning, during an outflow phase of the pumping cycle, the valve to a second pumping position to establish a fluid contact between the first aspiration cavity and the outlet tube without having a fluid connection between the inlet tube and the first aspiration cavity, moving, during the outflow phase, the first piston to decrease the volume of the first aspiration cavity is disclosed.

In a third exemplary aspect, a valve apparatus is disclosed for use in a fluid delivery system having an inlet tube and an outlet tube, the valve apparatus comprising a cylindrical base portion having a top end and a bottom end, the bottom end having a priming channel notch and a first and a second pumping channel notches and a cylindrical top portion having a proximal end connected to the top end base portion and a distal end having a handle, wherein the first and the second pumping channel notches are positioned circumferentially and are spaced apart from each other such that when one of the first and the second pumping channel notches is positioned to make a fluid contact between an aspiration cavity and either the inlet tube or the outlet tube, the other pumping channel notch does not make a fluid contact between the aspiration cavity and the inlet tube or the outlet tube, and wherein the first and the second pumping channel notches are vertically offset from the priming channel notch such that if the priming channel notch is in fluid contact with the inlet tube and the outlet tube, the first and the second pumping channel notches are not in fluid contact with the inlet tube and the outlet tube, and if the first and the second pumping channel notches are in fluid contact with the inlet tube or the outlet tube, the pumping channel notch is not in fluid contact with the inlet tube and the outlet tube and wherein the priming channel notch is sufficiently wide to establish a fluid connection between the inlet tube and the outlet tube.

The foregoing and other features, aspects and advantages of the embodiments of the present disclosure will become more apparent from the following detailed description and accompanying drawings.

DETAILED DESCRIPTION

The embodiments of the present invention address and solve problems related to medical fluid delivery systems. In particular, embodiments of the disclosure overcome limitations of previous fluid delivery pumps. The disclosed embodiments achieve this, at least in part, by providing a valve that delivers fluid from an inlet tube to an outlet tube. For example, in certain embodiments, the valve can be positioned in a priming position by a user. When the valve is in this priming position, a priming channel notch allows passage of fluid from the inlet tube to the outlet tube. The user then moves the valve into a pumping position. After the user moves the valve into the pumping position, the user can then activate an external electromechanical pump that is coupled with the valve. The external electromechanical pump rotates the valve between two pumping positions. In the first position, a pumping channel notch of the valve fluidly connects the inlet tube to an aspiration cavity. In the second position, the pumping channel notch is in fluid contact with the outlet tube. By toggling position of the rotary valve, the external electromechanical pump can thus transfer fluid from the inlet tube to the aspiration cavity, and then from the aspiration cavity to the outlet tube. In both steps, transfer of fluid is facilitated by reciprocating movement of a piston coupled to the aspiration cavity. In certain embodiments, the valve has a priming channel notch vertically offset from the pumping channel notches. In such embodiments, a user can set the valve to be in a pumping or a priming position by push/pull manipulation of the valve.

Figure 1:
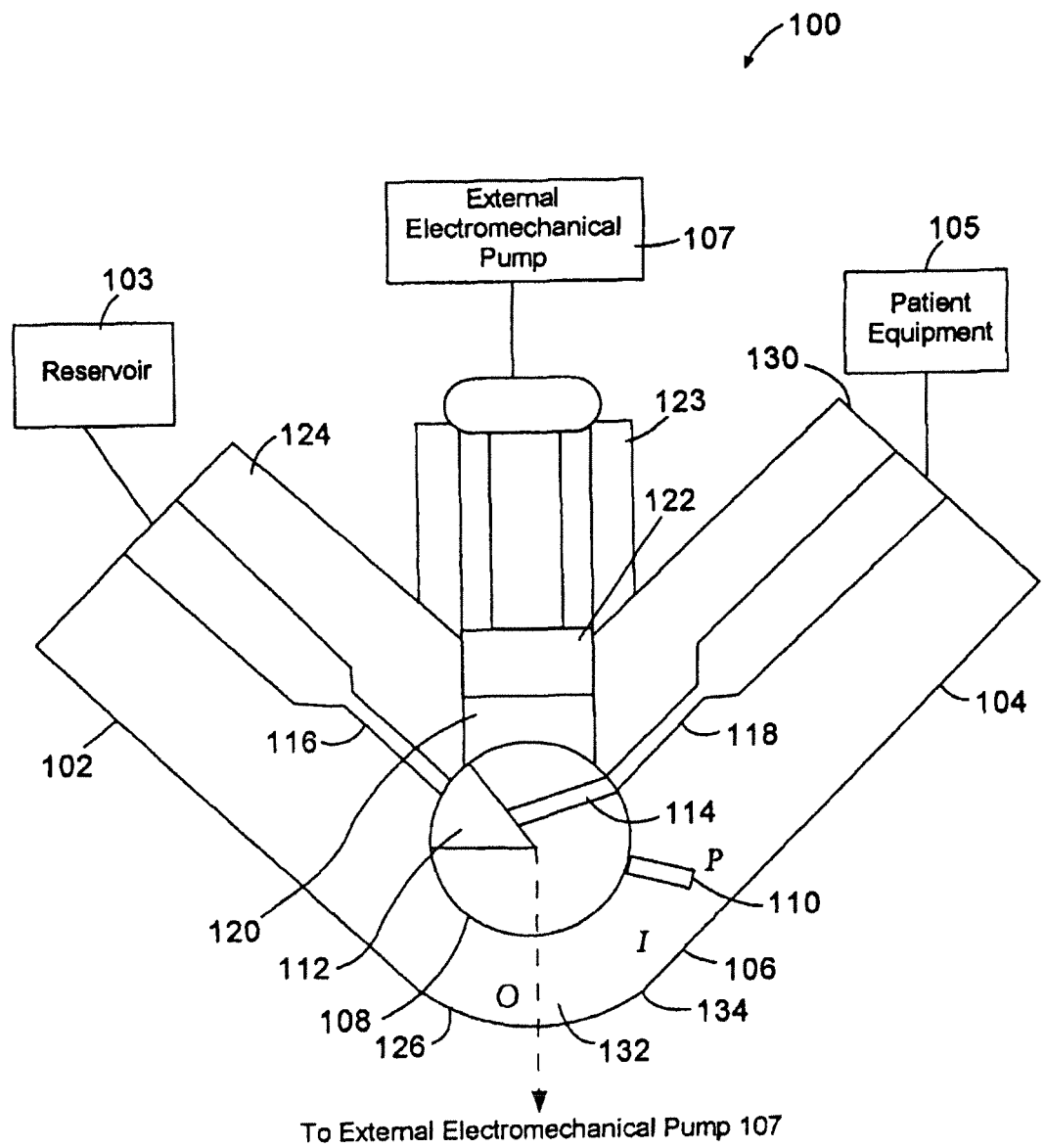
FIG. 1 is a cross-sectional view of a portion fluid delivery system, showing a valve in a priming position, in accordance with embodiments of the present disclosure.

FIG. 1 is a cross-sectional view of a fluid delivery apparatus 100 showing an inlet tube 102 and an outlet tube 104, each having a proximal end 124, 130 and a distal end 126, 134, angularly connected to each other at their distal ends 126, 134, forming an angular joint 106. The angular joint 106 has an internal cavity 132 in which a rotatable valve 108 is inserted. A handle 110 fitted on the valve 108 is accessible external to the wall 134 of the angular joint 106 and therefore not in direct contact with the fluid flowing through the inlet and the outlet tubes. The handle 110 may be rotated by a user to position the valve to a priming position as described below. The valve 108 is fitted with a wedge-shaped notch 112 and a priming tubule 114. The handle 110 can be moved to one of three positions (not all shown in FIG. 1): P (for priming), I (for fluid-in) and O (for fluid-out). The handle 110 is shown in the P position in FIG. 1.

When the handle 110 is in the P position, as shown in FIG. 1, the wedge-shaped notch 112 is fluidly connected with fluid channel 116 of the inlet tube 102, and the priming tubule 114 is aligned with the fluid channel 118 of the outlet tube 104, allowing fluid to flow from a reservoir 103 connected to the inlet tube 102 to flow through the priming tubule 114 of the valve 118 to a patient or equipment 105 connected to the outlet tube 104. It is well-known in the art that a fluid delivery line has to be primed to vent air from the line, before delivery of the fluid to a patient can begin. For use, a user turns the handle 110 (or other means provided) to the priming position P to prime the fluid pump 100. In certain embodiments, the priming position P for the handle 110 may be indicated on the exterior of the fluid pump 100 by an exterior mark, making it convenient for a user to simply turn the handle 110 so that it is aligned with the exterior mark. In certain embodiments, a user may employ gravity to prime the fluid pump 100. To perform priming, a user turns the handle 110 to the P position and employs gravity to draw out fluid from the reservoir 103 to the outlet tube 104. Upon completion of priming, the user can then turn the handle 110 to a pump position (I or O, preferably I). As described next, when the handle 110 is turned to a pump position, the direct connection between the inlet tube 102 and the outlet tube 104 is broken, and fluid delivery can only be performed by rotating the valve 108 between the pumping positions I and O, as further described below.

Figure 2:
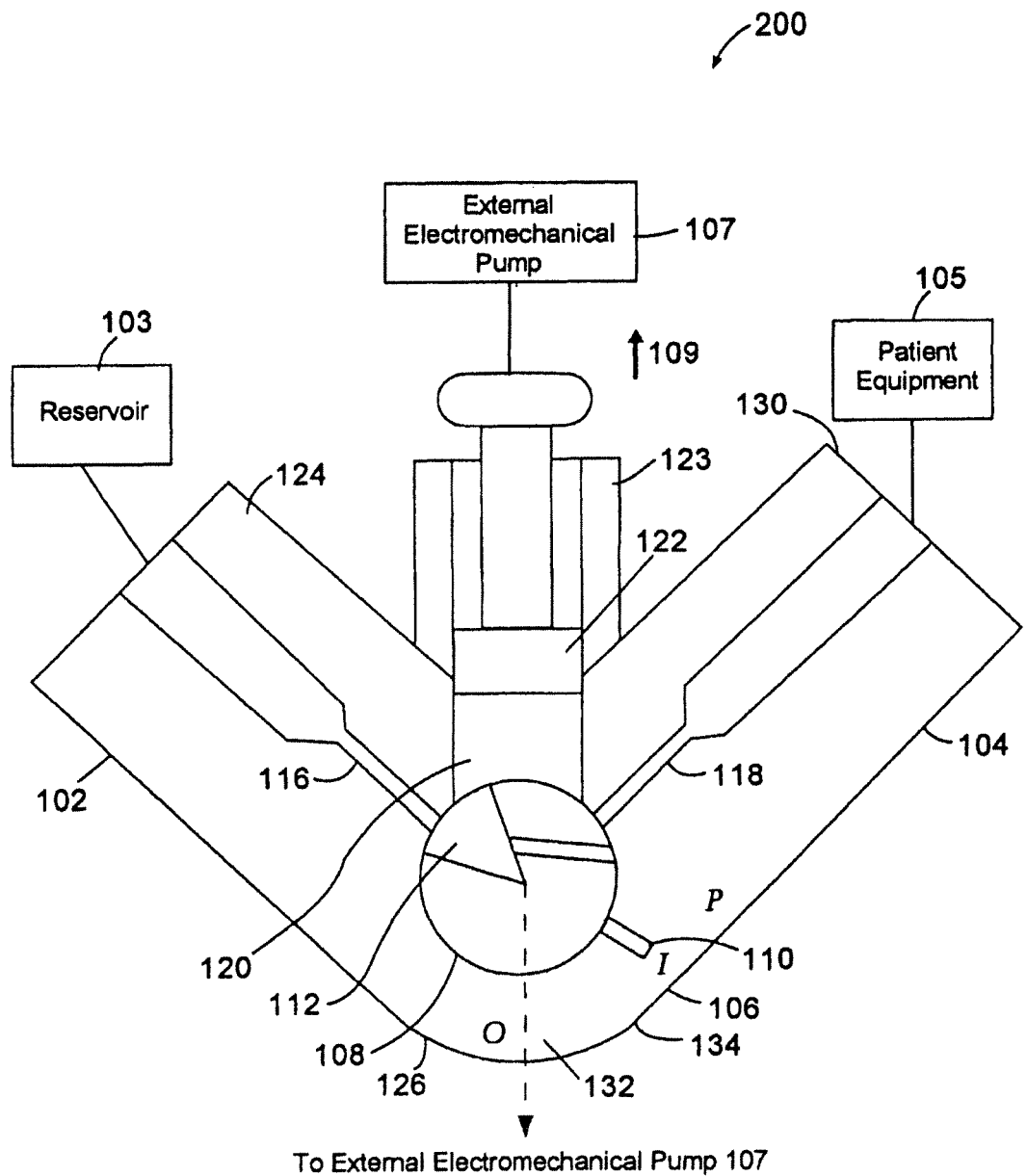
FIG. 2 is a cross-sectional view of the valve of FIG. 1, showing the valve in a first pumping position, in accordance with embodiments of the present disclosure.

FIG. 2 is a cross-sectional view of the fluid pump 100 that shows the operation of the fluid pump 100 with the handle 110 in the I position, and the pump 100 already primed by the user, as described above. When the handle 110 is in the I position, the wedge-shaped notch 112 is still aligned with the inlet tube 102. The width of the wedge-shaped notch 112 is chosen such that it is in contact with both the inlet tube 102 and the chamber 120 when the handle 110 is in the I position. A piston 122 is pulled outwardly in the direction of arrow 109 by an external electromechanical pump 107, thereby increasing volume of the chamber 120. Because the wedge-shaped notch 112 is in fluid contact with both the inlet tube 102 and the chamber 120, as a result of the expansion of the volume of the chamber 120, fluid from the reservoir (not shown in the figure) will enter the chamber 120. Note that because handle 110 is in the I position, the priming tubule 114 has rotated into a position in which it is not fluidly connected with the outlet tube 104. Therefore, fluid does not flow out from the wedge-shaped notch 112 and the chamber 120 through the priming tubule 114. After the piston 122 reaches its maximum pull-out position, the external pump 107 then begins moving piston 122 in the direction of arrow 111 and synchronized with this, the external pump 107 electromechanically rotates the valve 108 such that the handle 110 will move to the O position.

The external pump 107 may couple to the various moving parts described above (e.g. the piston 122, the valve 108) in a variety of ways. Some examples are listed here for illustrative purpose only and configurations described in the present disclosure may be combined with other known or future coupling mechanisms. In certain embodiments, the external pump 107 may use a claw foot design that the user hooks under the handle of the piston 107. In certain embodiments, the external pump 107 may fit into the piston 122 by sliding a pin into a press fit hole on the piston 122 and locking the external pump 107 to the piston 122. In certain embodiments, a user may drop the fluid delivery apparatus 100 into a pump 107 and the pump 107 may then find the piston 122 and couple to it.

In certain embodiments, a user may turn the valve 108 to a specific position and load the fluid delivery apparatus 100 into an external pump 107. For example, in certain embodiments, the external pump 107 may have a pump cavity configured such that handle 110 only fits into the external pump 107 one way so the external pump 107 cannot be misloaded. In certain other embodiments, an external pump 107 may "find" the handle 110 via a rotating pin that eventually hits the handle 110 and homes the valve 108 to a starting position. In certain embodiments, a feature affixed to the handle 110 (e.g., a screwdriver slot or a pin hole) is used as the locating feature by the external pump 107. Various other embodiments of the external pump 107 and the valve 108 for rotating the valve are possible.

Figure 3:
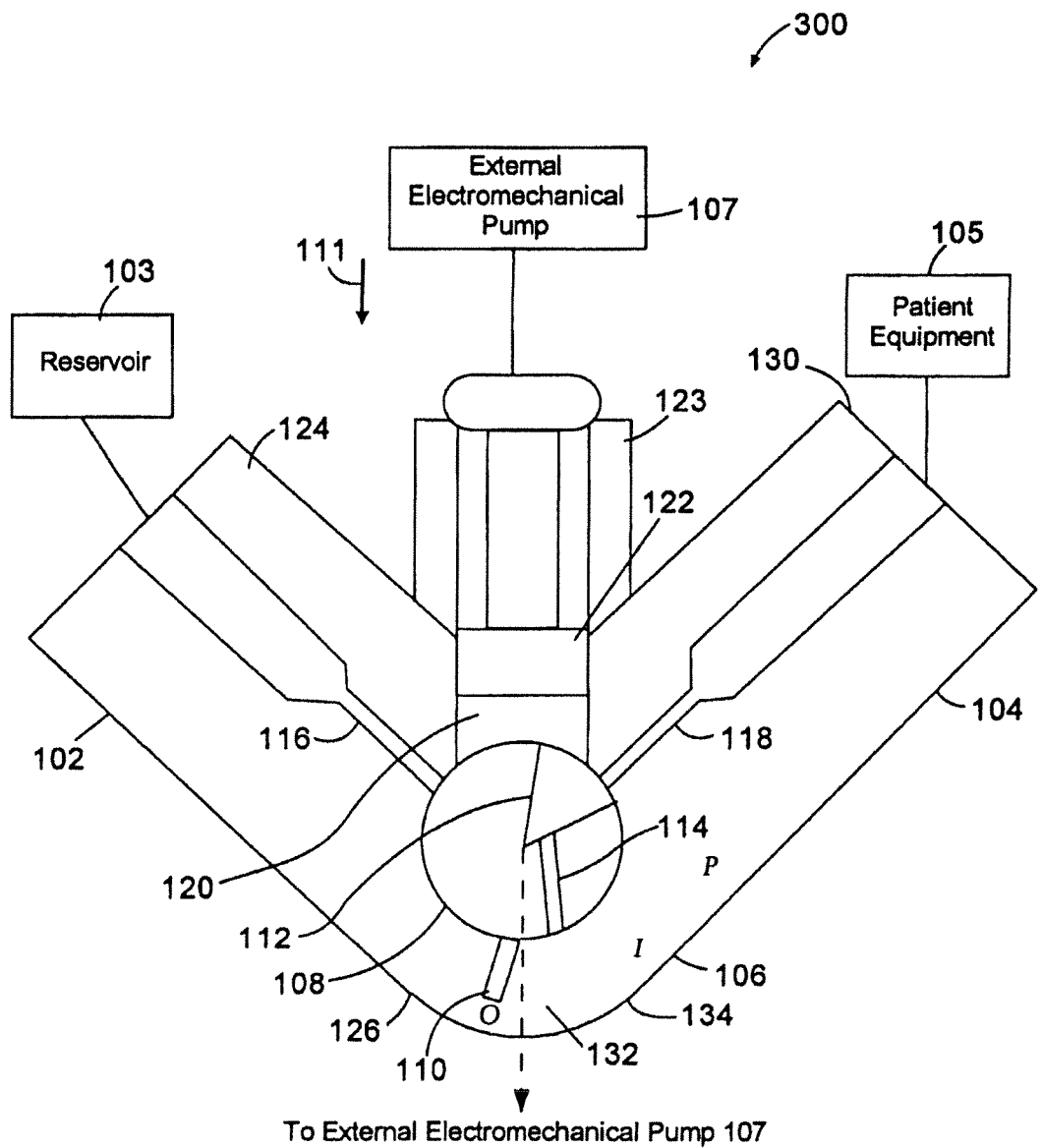
FIG. 3 is a cross-sectional view of the fluid delivery system of FIG. 1, with the valve in a second pumping position, in accordance with embodiments of the present disclosure.

FIG. 3 is a cross-sectional view of the fluid pump 100 in FIG. 1, with the valve 108 in the O position. In this position O, the chamber 120 is filled with fluid. Because the valve 108 has rotated, the inlet tube 102 is now cut off from any fluid contact with the chamber 120. However, because of the rotation of the valve 108, the wedge-shaped notch 112 is now in fluid contact with the outlet tube 104 and the chamber 120. Therefore, as the piston 122 is moved downwardly along arrow 111, the accumulated fluid from the chamber 120 is expelled into the fluid channel 118 of the outlet tube 104. In this position O, the priming tubule 114 is not in fluid contact with the inlet tube 102, the chamber 120 or the outlet tube 104, thereby not causing any fluid leakage from the priming tubule 114.

When the piston 122 reaches its maximum downward position shown in FIG. 3, substantially all of the fluid from the chamber 120 will have been expelled into the fluid channel 118 of the outlet tube 104. The external electromechanical pump 107 then begins moving the piston 122 outwardly again in the direction of arrow 111 and simultaneously rotates the valve 108 to the I position as depicted in FIG. 2, thereby repeating the process of filling the chamber 120 with fluid from the inlet tube 102 again.

Once the fluid pump 100 is primed by a user, the valve 108 can then be toggled back-and-forth by the external pump 107 between positions I and O for pumping fluid from the inlet tube 102 to the outlet tube 104. This toggling operation can be described in terms of a pump cycle. A pump cycle begins with the valve 108 in the I position and ends with the valve in the I position, having moved once to the O position during the pump cycle. Practitioners of the art can recognize that in one pump cycle, the pump 100 delivers fluid with volume approximately equal to the displacement volume of piston 122, also referred to as the piston's aspiration capacity, from the inlet tube 102 to the outlet tube 104. The duration of a pump cycle is controlled by an external pump mechanism 107 that controls the rate of the back-and-forth movement of the valve 108 between the I and the O positions. It can be appreciated by one skilled in the art that this mechanism delivers a fixed volume of fluid per pump, cycle, substantially equal to the aspiration capacity of the piston 122. Furthermore, because fluid movement from either inlet tube 102 to the chamber 120 or the chamber 120 to the outlet tube 104 is performed when the other side is shut off from fluid contact with the chamber 120, the fluid volume delivered per pump cycle is substantially independent of pressure changes on the inlet tube 102 or the outlet tube 104 caused by, inter alia, changing the height of the reservoir with respect to the patient.

Figure 4:
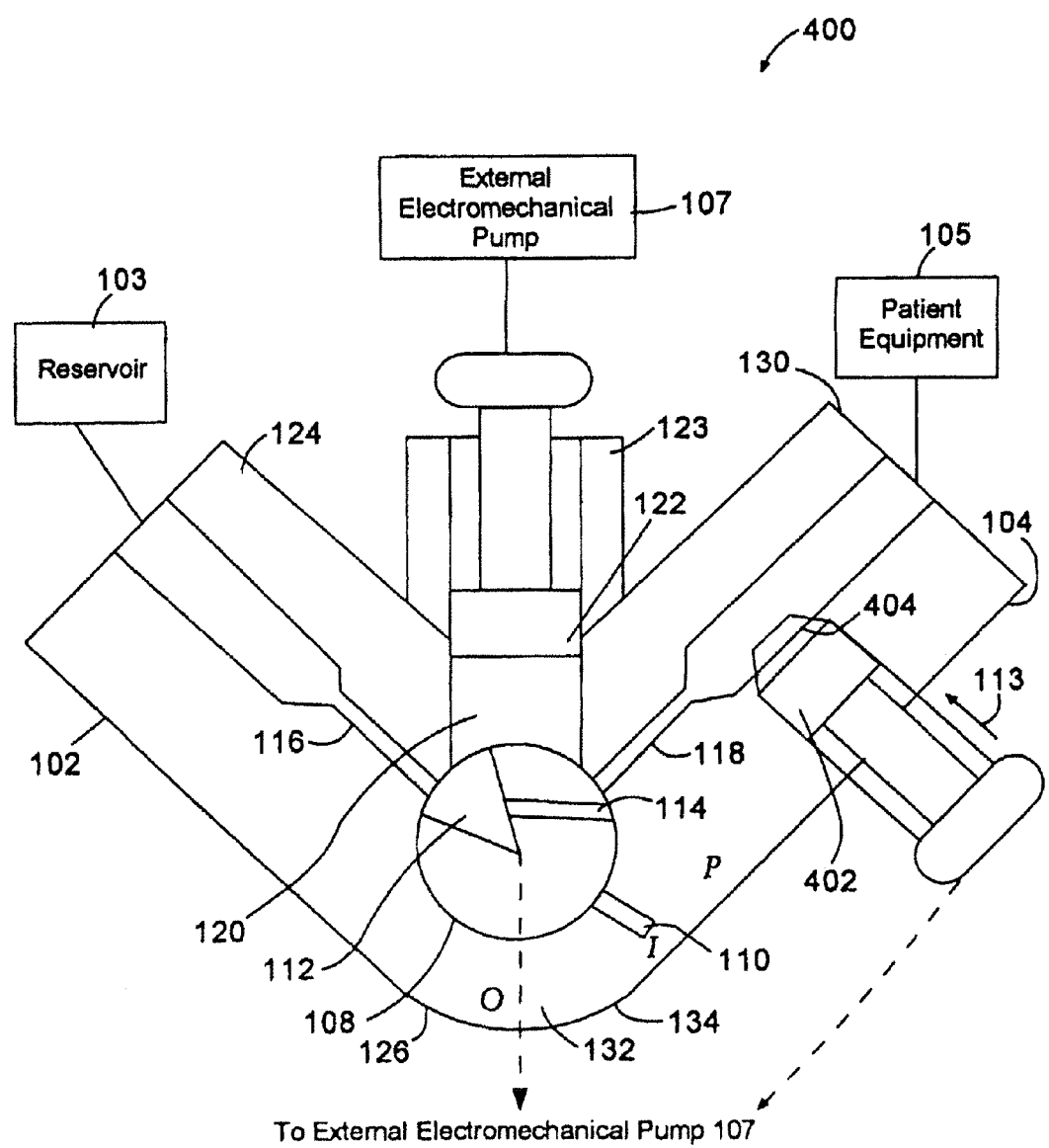
FIG. 4 is a cross-sectional view of a fluid delivery system, showing a two-piston arrangement, in accordance with embodiments of the present disclosure.

FIG. 4 is a cross-sectional view of another embodiment of a fluid pump apparatus 400. Compared to the fluid pump 100, this embodiment includes an additional piston 402 fitted in an enclosure connected to the outlet tube 104. The piston 402 forms a chamber 404 in fluid contact with the fluid channel 118 of the outlet tube 104. The external electromechanical pump 107 may time push/pull movement of the piston 402 to be "out-of-phase" with respect to push/pull movement of the piston 122. Therefore, when piston 122 is pushing fluid out of chamber 120 into the outlet tube 104, piston 402 is being pulled outwards, thereby increasing volume of the chamber 404. This results in a volume of fluid equal to the aspiration capacity of the piston 402, typically less than the aspiration capacity of the piston 122, accumulating in the chamber 404 instead of being delivered from chamber 120 to the patient.

When the valve 108 is in the I position, and the piston 122 is drawing fluid in from the inlet tube 102 into the chamber 120, no fluid is transferred from the chamber 120 to the fluid channel 118 of the outlet tube 104. The external pump 107 pushes the piston 402 in the direction of arrow 113 so that the fluid aspired in the chamber 404 is expelled into the fluid channel 118 for delivery to the patient. As a result of this movement of the piston 402 synchronized with movement of the piston 122, fluid from the chamber 120 is delivered to a patient in two steps. In the first step (when valve 108 is in the O position), fluid is delivered to a patient with volume equal to the aspiration capacity of the pump 122 minus the aspiration capacity of the pump 402. In the second step (when the valve 108 is in the I position), fluid is delivered to the patient with volume equal to the aspiration capacity of the pump 402. As can be appreciated by practitioners of the art, addition of the piston 402 as in the fluid pump 400 results in reduced pulsation of fluid delivery rate. This reduced pulsation can be achieved by choosing the aspiration capacity of the piston 402 to be smaller than the aspiration capacity of the piston 122. This ensures that not all fluid from the chamber 120 is siphoned into the chamber 404 in the first phase of the pump cycle. In a preferred embodiment, the aspiration capacity of the pump 402 is 50% of the aspiration capacity of the pump 122. This capacity results in about an equal amount of fluid being delivered in each phase of a pump cycle, thereby resulting in a near constant rate of flow throughout a pump cycle. Persons skilled in the art will recognize that with the introduction of a second piston 402, the time required to turn the valve 108 and refill the first piston 122 is no longer a factor in the delivery cycle because the second piston 402 is able to provide fluid to the patient while refill of the first piston 122 is taking place.

Still referring to FIG. 4, an external pump 107 may synchronize the pistons 122, 402 as follows. Initially, both pistons start bottomed out against their respective chambers 120, 404. First, the fluid delivery apparatus 100 is primed with the valve 108 in the P position. Then, the valve 108 is turned to the I position while the first piston 122 is moved outward in the direction of arrow 109. Next, the valve 108 to the O position and simultaneously first piston 122 is pushed in the direction of arrow 111 while the second piston 402 is simultaneously pulled back. In certain embodiments, the second piston chamber 404 is half the size of the first, and the second piston 402 effectively removes half of the volume that the first piston 122 delivered and stores it for a later delivery. Now the valve 108 rotates back to the I position. The second piston 402 moves inwards in the direction of arrow 113 to deliver the fluid removed, and the first piston 122 moves along arrow 111 to aspirate the next bolus of fluid. The valve 108 then turns back to the O position, and again the first piston 122 delivers to the patient while the second piston 402 retracts to store half of the volume to be delivered on the next fill cycle for the first piston 122. Such operation of the two pistons 122, 402 creates a less pulsatile flow experience for the patient and smoothes out the fluid delivery process because the "wait time" for the valve 108 to turn back and forth between pulses does not alter the fluid flow.

It will be appreciated by practitioners of the art that the simplicity of the fluid pump embodiments described in FIGS. 1 through 4 lends itself to an implementation with relatively few components. In a preferred embodiment, the fluid pump 100 is implemented using four components. One component is a conduit containing an inlet and an outlet for tubing to bond to, and two chambers between the inlet and the outlet for pistons (a single chamber for pulsating flow embodiment). This component also contains an area where the valve can be fitted. The second component is a valve that is designed to control the direction of flow by toggling back-and-forth. The third component is the piston that resides on the angular joint. In a preferred embodiment, the piston is a two-shot piston with a compliant surface that moves inside a cylinder and has a rigid handle that can be grasped by an electro-mechanical pumping interface (not shown in FIGS. 1 through 4). The fourth component is the optional second piston/chamber combination to allow the pump to produce a continuous flow. The embodiments described above do not preclude integration of the fluid pump apparatus with a self-sealing injection site such as a SmartSite™ needle-free valve or a Texium™ male luer product from Cardinal Health Incorporated.

Figure 5:
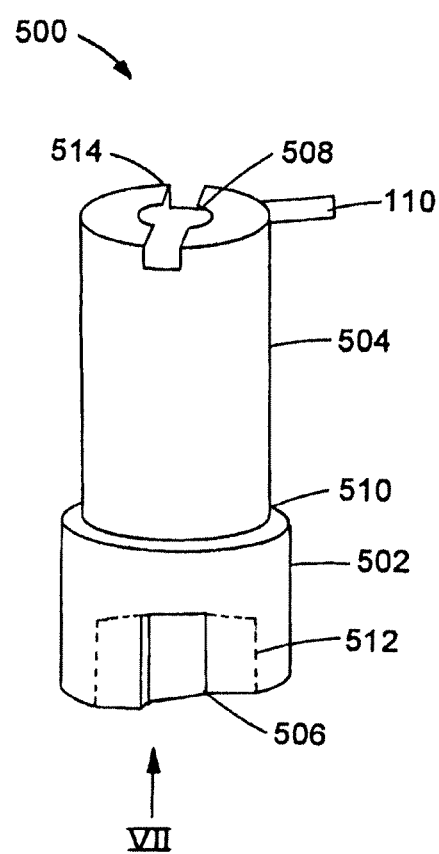
FIG. 5 is a perspective view of a valve, showing a pumping notch, in accordance with embodiments of the present disclosure.

FIG. 5 is a perspective view of another embodiment 500 of the valve 108, depicted in isolation from the fluid pump 100. In this embodiment, the valve 500 comprises a base portion 502 and a top portion 504. The valve 108 is fitted with a handle 110, used for rotating the valve 108, as described previously. This valve embodiment 500 differs from the previously discussed valve embodiment 108 in that no pumping tubule 114 is provided in this embodiment. Instead, the priming and pumping actions are achieved by providing priming and pumping notches around the periphery of the base portion 502 as described next. The base portion 502 is provided with a pumping notch 506 around its perimeter. The base portion 502 is also provided with a priming channel notch 512, shown in FIG. 5 with dashed lines because it is on the back side of the view. Both the pumping notch 506 and the priming channel notch 512 are at the end of the base portion 502 that is farther away from the top portion 504. The angular width of the pumping notch 506 is less than the angular width of the priming channel notch 512. The angular width of the pumping notch 506 is chosen such that it is long enough to connect the fluid channel 116 or 118 to the chamber 120, but does not connect the fluid channels 116 and 118 to each other. In contrast, the angular width of the priming channel notch 512 is long enough to connect the fluid channels 116 and 118 to each other so that fluid can pass from the inlet tube 102 to the outlet tube 104 during priming.

Still referring to FIG. 5, the top portion 504 is generally cylindrical in shape, with a proximate end 510 in contact with the base portion 502 and a distal end 508 having a notch 514 in which an external mechanism, such as an electromechanical motor (not shown in FIG. 5), can fit within and rotate the valve 500. When the valve 500 rotates, the base portion 502 rotates while being in contact with fluid and the chamber 120 and the top portion 504 rotates while being out of contact with the casing of the chamber 120 to reduce friction during pumping. Thus, the wear and tear experienced by the portions 502, 504 is different. To suitably cope with the wear and tear, these portions can be made from different materials. In certain embodiments, the base portion 502 is made of a soft sealing material that is injection molded onto the top portion 504, which is made of a rigid wear-resistant material. The soft sealing material can then be injection-molded over the rigid material, thereby giving a simple yet durable valve configuration.

Figure 6:
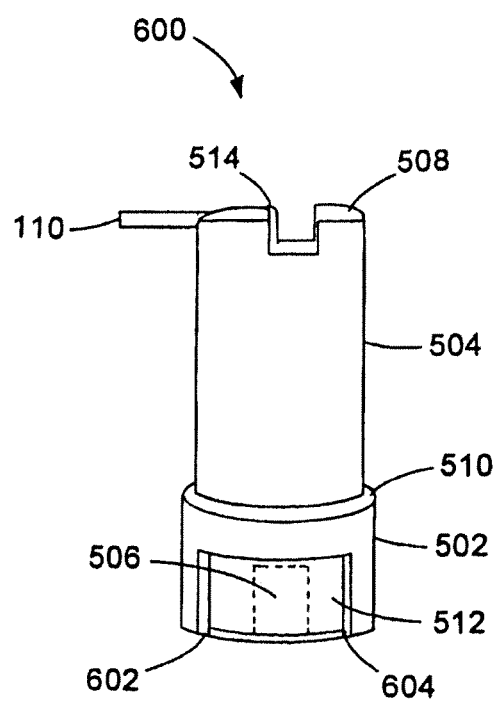
FIG. 6 is a perspective view of the valve of FIG. 5, showing the priming notch, in accordance with embodiments of the present disclosure.

FIG. 6 is a perspective view 600 of the rotary valve 500 rotated 180 degrees from the view in FIG. 5. The priming channel notch 512 now is depicted in front, showing its two ends 602 and 604. The pumping notch 506 is now depicted in dashed lines because it is on the back side of the view.

Figure 7:
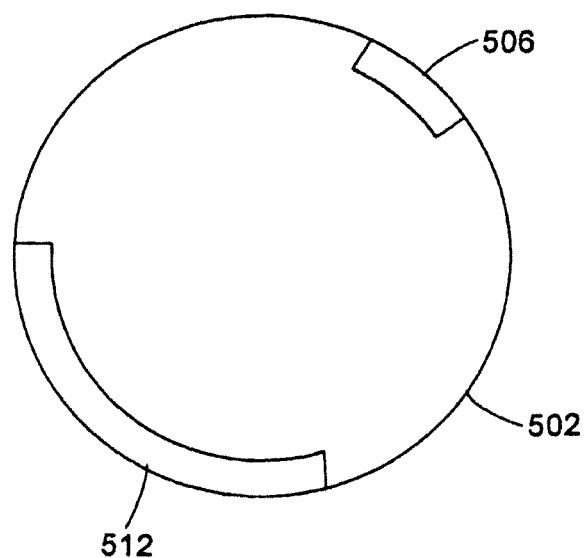
FIG. 7 is a plan view of the valve of FIGS. 5 and 6, showing underside of the valve, in accordance with embodiments of the present disclosure.

FIG. 7 is a bottom view of the valve 500 in the direction of arrow VII in FIG. 5. The priming channel notch 512 and the pumping notch 506 are visible around the circumference of the base 502. In certain embodiments, the depths of both these notches 506 and 512 may be identical. In certain other embodiments, the notches 506 and 512 may be chosen to have different depths responsive to fluidity properties of the fluid intended to be pumped through the pump 100. For example, in a fluid pump 100 designed for fluids with higher viscosity, a wider and shallower pumping notch 506 may be provided to overcome surface adhesion of the fluid. Another advantage to adjusting the height of the notch is to increase or reduce the flow rate to a range that is clinically applicable. Generally speaking, a deeper or wider notch provides less fluid flow resistance, and a more shallow or narrower notch provides more fluid flow resistance. In certain embodiments, the size for notch 506 may be chosen to be different from the size of priming channel notch 512 if, inter alia, it is clinically preferred to prime at a fast flow rate through priming channel notch 512, but to pump to the patient with some resistance that could be detected by back pressure to the piston 122 through notch 506. The priming channel notch 512 is wider than the pumping notch 506 for reasons discussed above.

Figure 8:
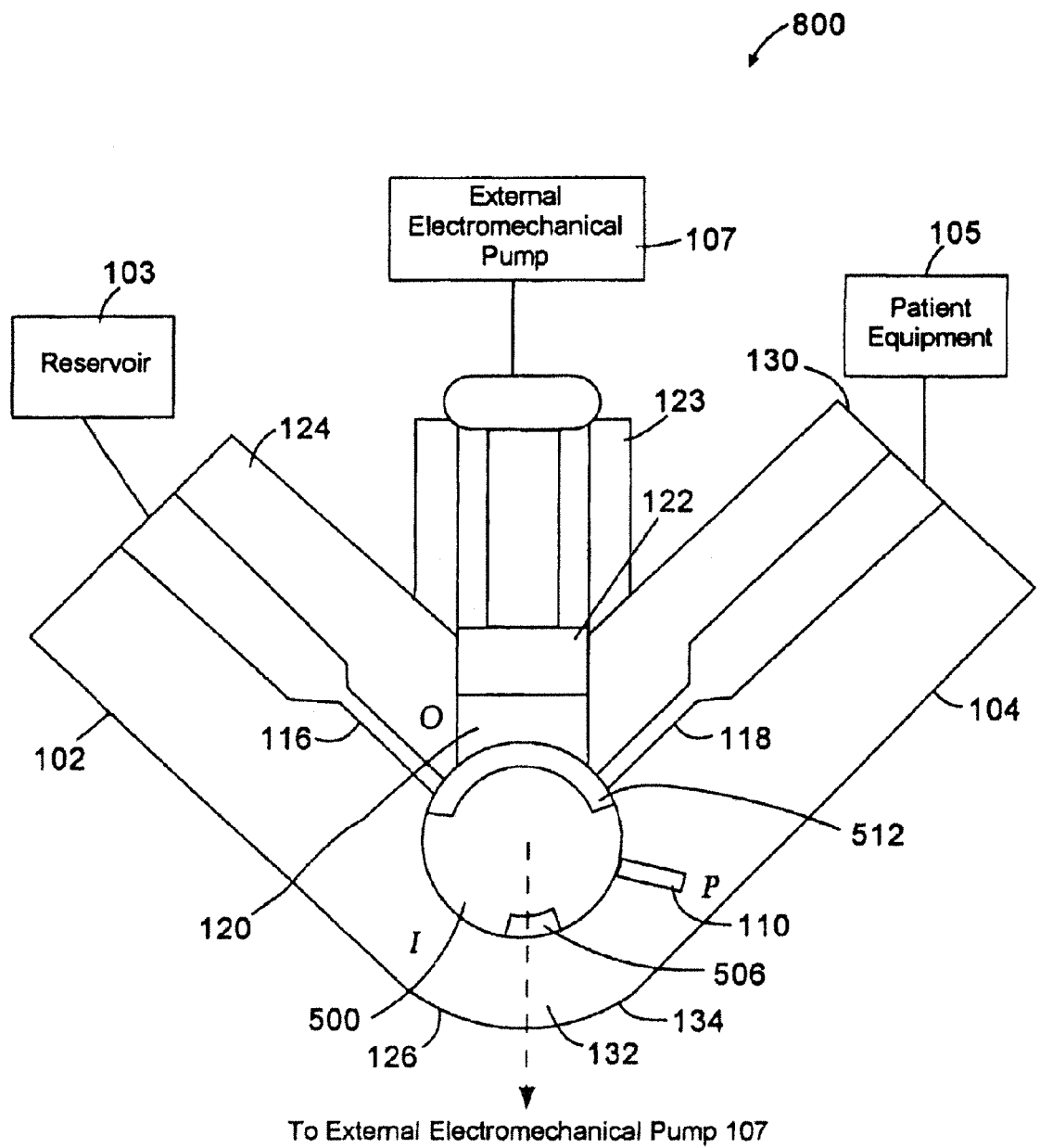
FIG. 8 is a cross-sectional view of a fluid delivery system, showing the valve in FIG. 5 in priming position, in accordance with embodiments of the present disclosure.

FIG. 8 is a cross-sectional view of an alternate embodiment of a fluid delivery apparatus 100. The fluid delivery apparatus 800 uses the valve embodiment 500 instead of the previously disclosed valve embodiment 108. FIG. 8 shows the valve 500 in the P position. As discussed before, the angular width of the priming channel notch 512 is wide enough to allow fluid from the fluid channel 116 pass to the fluid channel 118.

Figure 9:
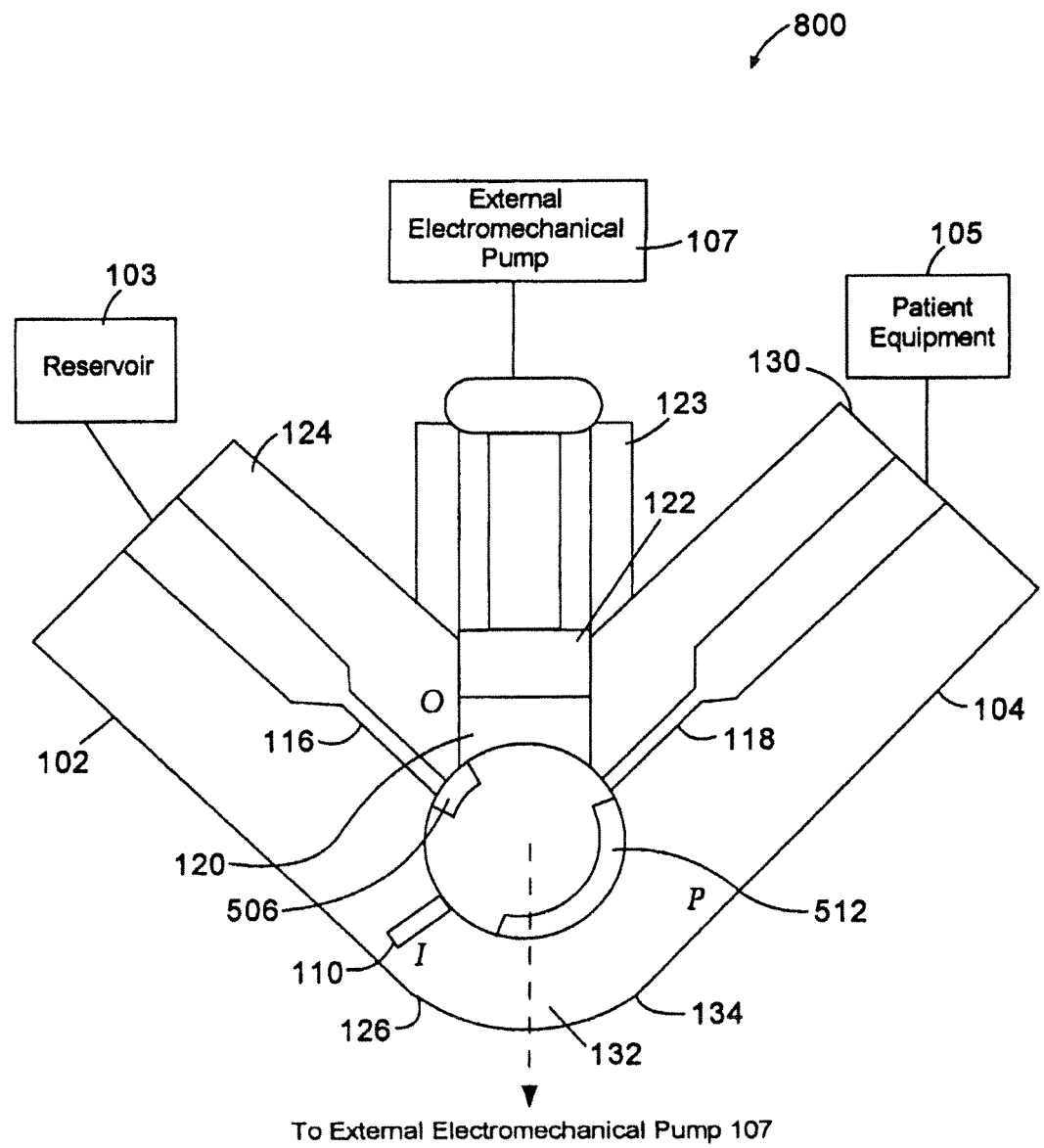
FIG. 9 is a cross-sectional view of a fluid delivery system, showing the valve in FIG. 5 in a first pumping position, in accordance with embodiments of the present disclosure.

FIG. 9 is a cross-sectional view showing the valve 500 in the I pumping position. In this position, the pumping notch 506 is aligned with the inlet tube 102 and the chamber 120. The pumping notch 506 is configured to be wide enough to allow fluid from the inlet fluid channel 116 to pass into the chamber 120. However the pumping notch 506 is narrow enough so that it does not also open into the outlet fluid channel 118. As previously described, when the valve 500 is in the I pumping position, the external electromechanical pump 107 will pull the piston 122 outwardly in the direction of arrow 109, thereby expanding volume of the chamber 120 and allowing fluid from the channel 116 to fill into the chamber 120. When the valve 500 is in the I position, the priming channel notch 512 has rotated away from the fluid channels 116 and 118 and the chamber 120, thereby not causing any fluid leakage through the priming channel notch 512.

Figure 10:
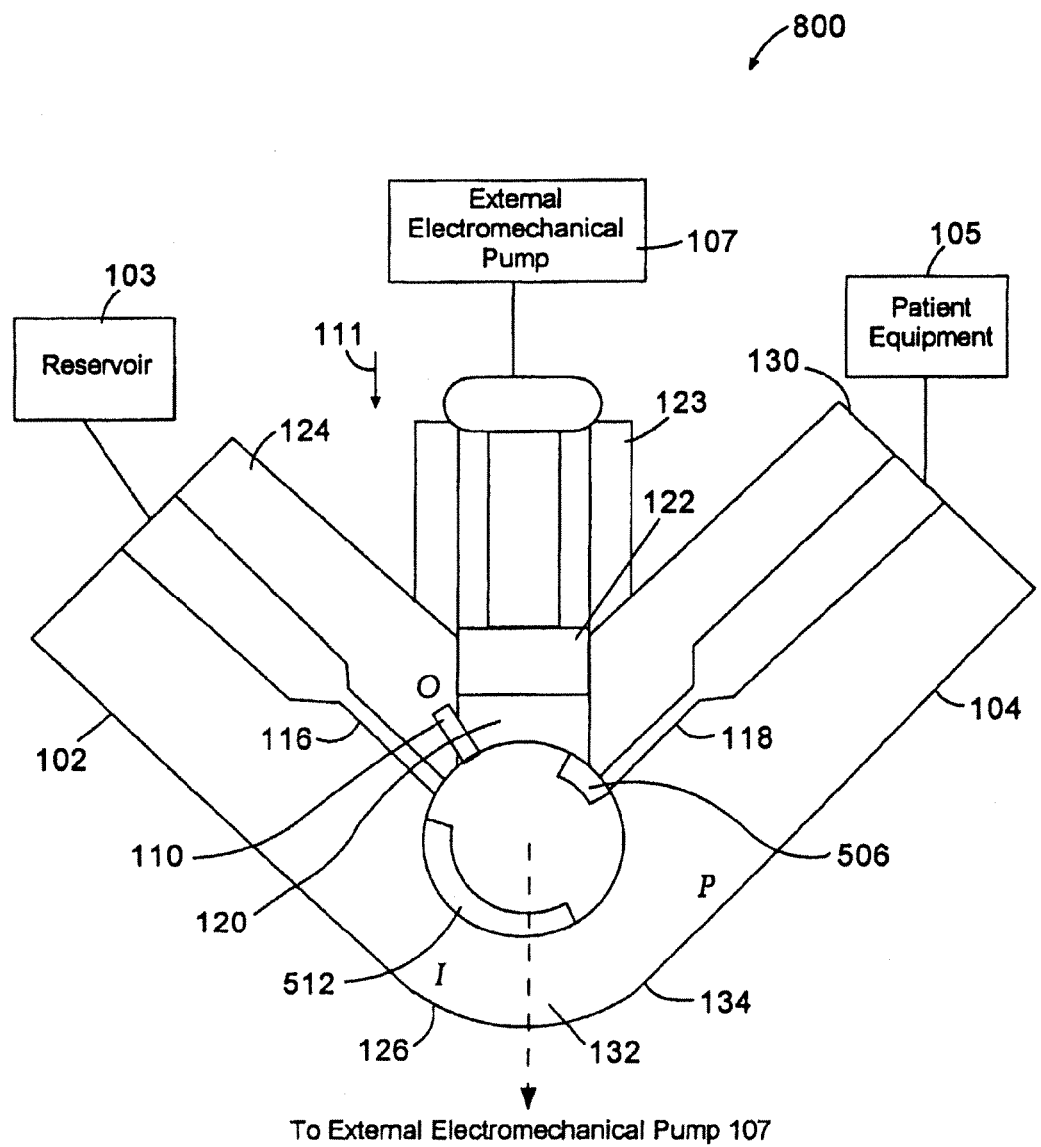
FIG. 10 is a cross-sectional view of a fluid delivery system, showing the valve in FIG. 5 in a second pumping position, in accordance with embodiments of the present disclosure.

FIG. 10 is a cross-sectional view of the fluid delivery apparatus 800 showing the valve 500 in the O pumping position. The pumping notch 506 is now in fluid contact with the chamber 120 and the fluid channel 118. In the O pumping position, the external pump (not shown in FIG. 10) pushes the piston 122 inwards thereby causing fluid from the chamber 120 to expel into the fluid channel 118. The priming channel notch 512 has rotated further, and is not in fluid contact with either channels 116, 118 or chamber 120, thereby not causing any fluid leakage directly through the priming channel notch 512. After the piston 122 is completely pushed inwardly in the direction of arrow 111 by the external electromechanical pump 107, the piston 122 then begins to be pulled out, with the valve 500 being put into the I pumping position, as depicted in FIG. 9. The fluid pump embodiment shown in FIGS. 8-10 delivers fluid from the inlet tube 102 to the outlet tube 104 by toggling the valve 500 between the I and the O pumping positions. One skilled in the art will recognize that certain embodiments of the valve 500 are possible in which the valve 500 has more than two pumping notches 502. In such embodiments, the valve 500 will be rotated such that fluid is first delivered from the inlet tube 102 into the chamber 120 and then expelled out of the chamber 120 to the outlet tube 104.

It will be appreciated by practitioners of the art that the valve 500 described above can be employed in certain fluid pump embodiments that includes a second piston fitted on the outlet tube 104, such as the piston 402 described above in the context of FIG. 4. In certain embodiments, valve 500 may be designed to form a reservoir between wall 134 and the bottom of the valve (element 502 in FIG. 7). The reservoir allows for fluid to move freely between the inlet tube 102 and the outlet tube 104, without getting trapped and growing bacteria or causing a loss of delivered fluid volume.

Figure 11:
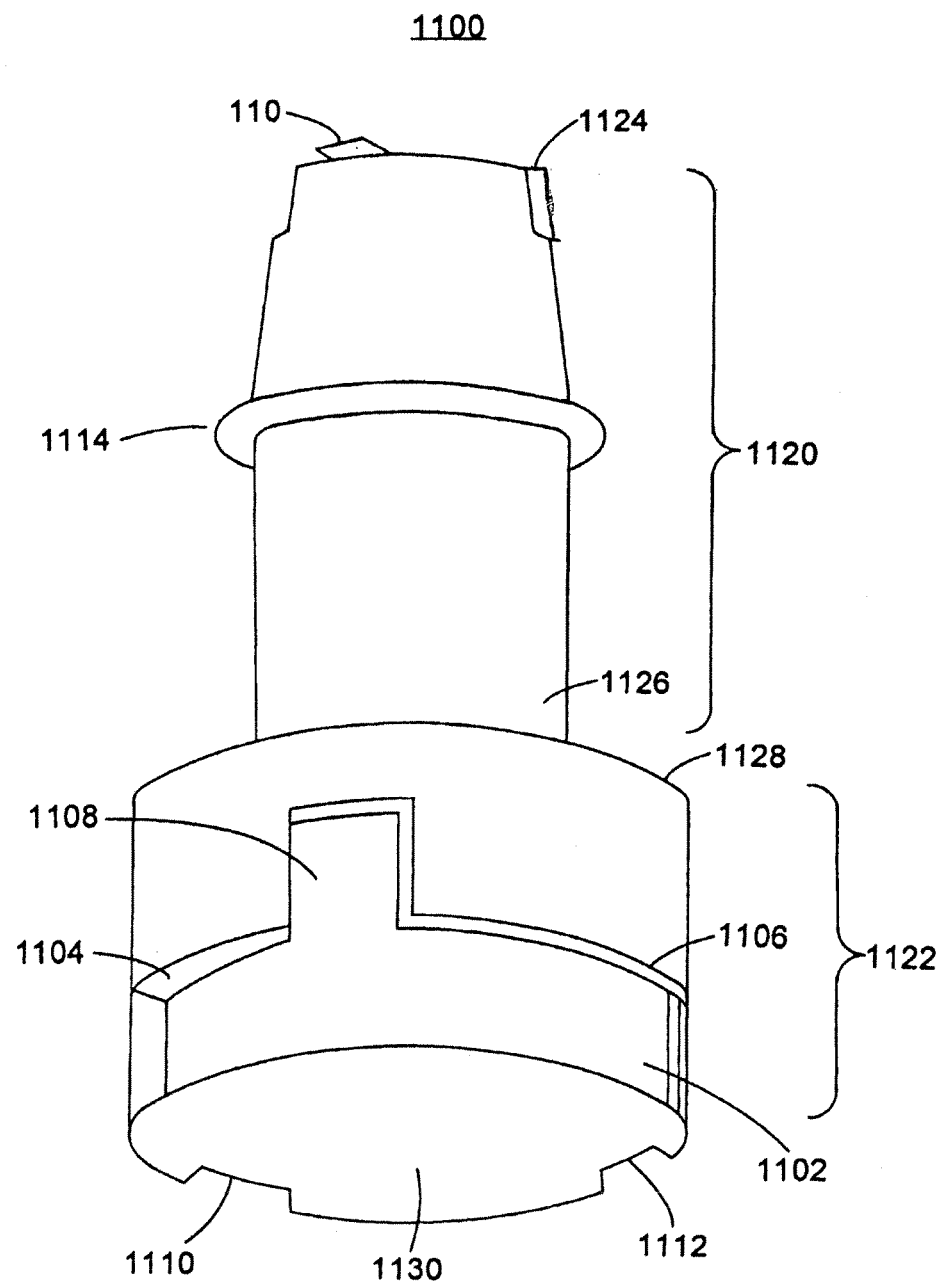
FIG. 11 is a perspective view of a valve in accordance with embodiments of the present disclosure.

FIG. 11 is a perspective view of another embodiment 1100 of a rotary valve useful with embodiment of the present disclosure. One aspect in which the embodiment 1100 differs from valve embodiments 108 and 500 is that valve 1100 is configured to allow operation of the fluid pump 100 with the valve 1100 rotating continuously instead of toggling back-and-forth. Such an embodiment may offer the advantage that a continuously rotating valve may expend less energy, thereby prolonging battery life of the fluid delivery system.

Still referring to FIG. 11, the rotary valve 1100 has a top portion 1120 and a base portion 1122. To facilitate rotation of the valve 1100, both the top portion 1120 and the base portion 1122 are generally cylindrical in shape. In the illustrated embodiment, the top portion 1120 has a diameter smaller than the bottom portion 1122. The bottom end 1126 of the top portion 1120 is attached to the top end 1128 of the base portion 1122. The top end 1124 of the top portion 1120 is fitted with a groove or other means (not illustrated) by which an external electromechanical system can engage with the valve 1100 to rotate it. The top portion 1120 is also fitted with a collar 1114 to limit the inward pushing movement of the valve 1100 during its operation as explained further below. Similarly, another mechanical feature, such as a ring 1116, could be added to prevent the outward retraction of the valve 1100 to prevent it from separating from the fluid delivery device 100. It is also possible to combine these mechanical features into one locking device, inter alia, a snap fit ring that moves up and down inside a column (not shown). The base portion 1122 will be positioned inside the angular joint 106 and will be in contact with the fluid. The bottom end 1130 of the base portion has a priming channel notch 1102 and three pumping channel notches 1108, 1110 and 1112. It is possible to have a primable fluid reservoir below feature 1130 in the mating component such that all the notches shown (1102, 1108, 1110, and 1112) are in constant communication with the reservoir to ensure no trapping of fluid in the device within the notches. In certain embodiments, the priming channel notch 1102 is deeper at one end 1104 and tapers off to being shallower at the other end 1106 to allow for manual flow speed control during priming. In other embodiments, the priming channel notch 1102 may have uniform depth throughout. The priming channel notch 1102 and the pumping channel notches 1108, 1110 and 1112 are spaced apart from each other. One of the pumping notches (1108) overlaps with the priming channel notch 1102, but is not as wide as the priming channel notch 1102 and extends beyond the priming channel notch towards the bottom end 1126 of the top portion 1120. The heights of the pumping channel notches 1108, 1110 and 1112 are greater than the height of the priming channel notch 1102. The angular widths of the pumping channel notches 1108, 1110 and 1112 are less than the angular width of the priming channel notch 1102 for reasons further explained below. It will be appreciated by those familiar with the art that the number of notches and widths and heights of the channel could all be adjusted as required to perform the clinically or electromechanically preferred amount of turning, delivering, and priming control.

Figure 12:
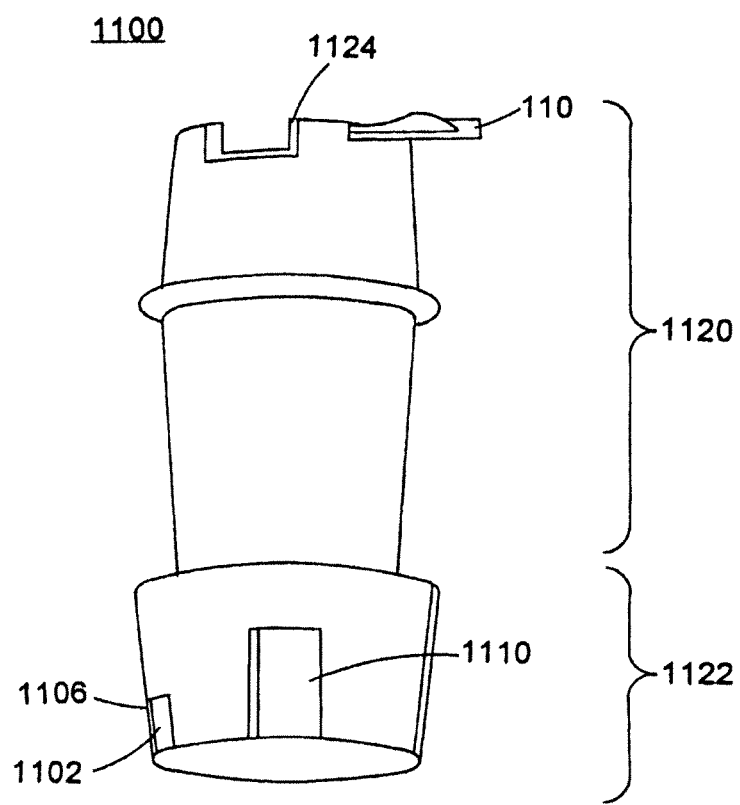
FIG. 12 is a perspective view of the valve of FIG. 11, showing a first pumping notch, in accordance with embodiments of the present disclosure.

FIG. 12 is a perspective view of the rotary valve 1100 shown in FIG. 11, rotated such that pumping notch 1110 is visible. The shallower end 1106 of the priming channel notch 1102 is visible also. The pumping notch 1110 is spaced apart from the priming channel notch 1102 and extends more towards the top portion 1120 than the priming channel notch 1102.

Figure 13:
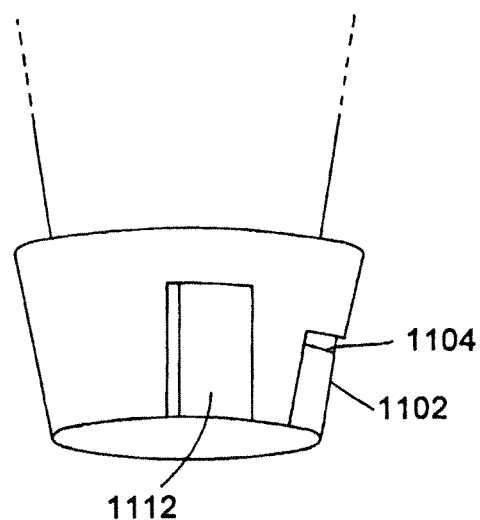
FIG. 13 is a perspective view of bottom portion of the valve of FIG. 11, showing a second pumping notch, in accordance with embodiments of the present disclosure.

FIG. 13 is a perspective view of the base portion 1122 of the valve 1100 shown in FIG. 11, rotated to show the pumping notch 1112. The deeper end 1104 of the priming channel notch 1102 is also visible. As noted before, the pumping notch 1112 is spaced apart from the priming channel notch 1102 and extends more towards the top portion 1120 than the priming channel notch 1102.

Figure 14:
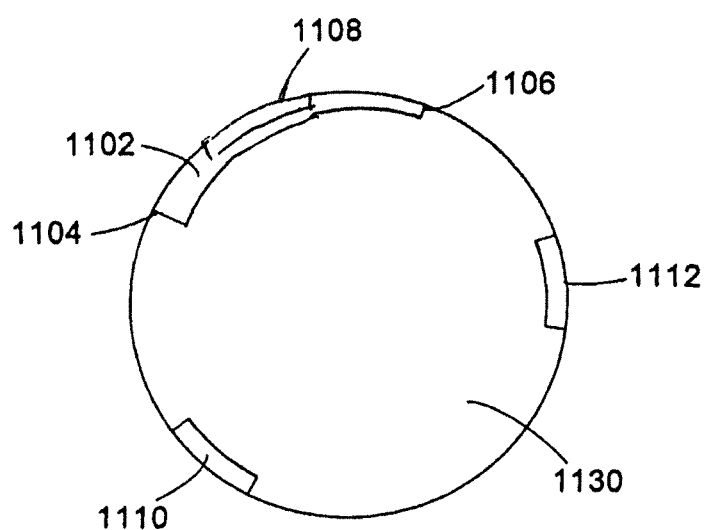
FIG. 14 is a plan view of the valve of FIG. 11, showing underside of the valve, in accordance with embodiments of the present disclosure.

FIG. 14 is a bottom view 1400 of the rotary valve 1100, showing exemplary relative positioning of the priming channel notch 1102 and the pumping notches 1108 around the circumference of the bottom end 1130 of the rotary valve 1100. In this view, the tapering of the priming channel notch 1102 from the deeper end 1104 to the shallower end 1106 can be better appreciated. The pumping notch 1108 is co-located with the priming channel notch 1102 as shown in FIG. 14.

Figure 15:
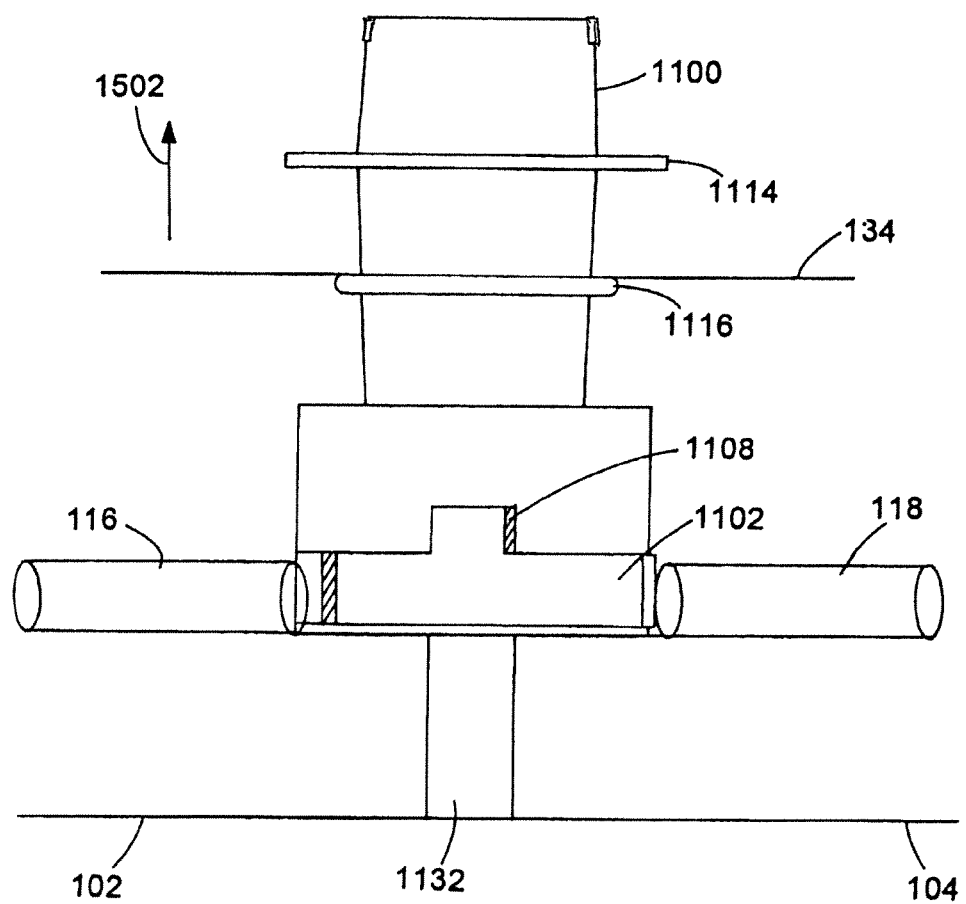
FIG. 15 is a cross-sectional view of a fluid delivery system incorporating the valve of FIG. 11, showing the valve pulled out to the priming position, in accordance with embodiments of the present disclosure.

FIG. 15 is a cross-sectional view 1500 of a fluid pump incorporating the valve 1100, showing the valve 1100 in the priming position. To move the valve 1100 into the priming position, a user first turns the valve 1100 to the priming position P and then pulls the valve out, in the direction of arrow 1502, to the priming position. The outward movement of the valve in the direction of arrow 1502 can be controlled by providing tactile feedback to the user such as stopping the outward movement when the base portion 1122 of the valve 1100 touches the wall 134. In certain embodiments, another ring 1116 can be provided on the valve 1100 below the ring 114 to stop outward movement of the valve 1100 when the valve 1100 reaches the desired position. When the valve 1100 is in the priming position, the priming channel notch 1102 is aligned with the fluid channels 116 and 118 of the inlet tube 102 and the outlet tube 104 respectively. The priming channel notch 1102 is wide enough to allow passage of fluid from fluid channel 116 to fluid channel 118, thereby achieving priming of the pump 100. Because the priming channel notch 1102 tapers in depth from the deep end 1104 to the shallow end 1106, a user can adjust the rate of fluid flow during the priming operation by turning the valve towards either the deeper end (to increase the flow) or the shallower end (to reduce the flow) during the priming operation.

Still referring to FIG. 15, a fluid reservoir 1132 below bottom 1130 is advantageously used to allow fluid to flow freely between the inlet tube 102 and the outlet tube 104. The volume of the fluid reservoir 1132 is controlled by the position of the valve 1100 with respect to the wall 134.

Figure 16:
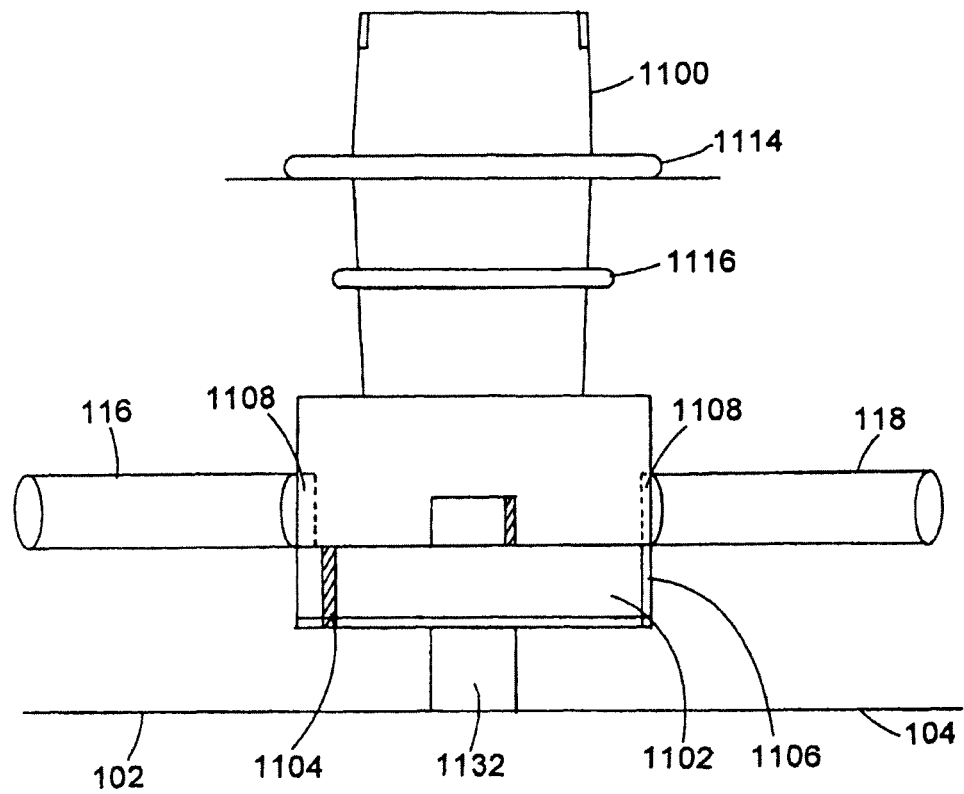
FIG. 16 is a cross-sectional view of a fluid delivery system incorporating the valve of FIG. 11, showing the valve pushed into a pumping position, in accordance with embodiments of the present disclosure.

FIG. 16 is a cross-sectional view of a portion of a fluid delivery apparatus incorporating valve 1100, showing valve 1110 in a pumping position. A user or the electromechanical pump 107 can place the valve 1100 in the pumping position by pushing the valve 1100 inwards. The collar 1114 stops the inward movement of the valve 1100 and provides a user with tactile feedback that the valve 1100 is set to the pumping position. The priming channel notch 1102 is now not vertically aligned with the fluid channels 116 and 118. Instead, the top parts of the pumping notches 1108, 110 and 1112 that extend beyond the priming channel notch 1102 are vertically aligned with the fluid channels 116 and 118. Thus, simply by pushing in the valve 1100, a user can change the valve 1100 from the priming to the pumping position and allow pumping of the fluid to commence through the fluid delivery apparatus 100 as further described below. With the valve 1100 in this position, fluid is also delivered through the reservoir 1132.

Figure 17:
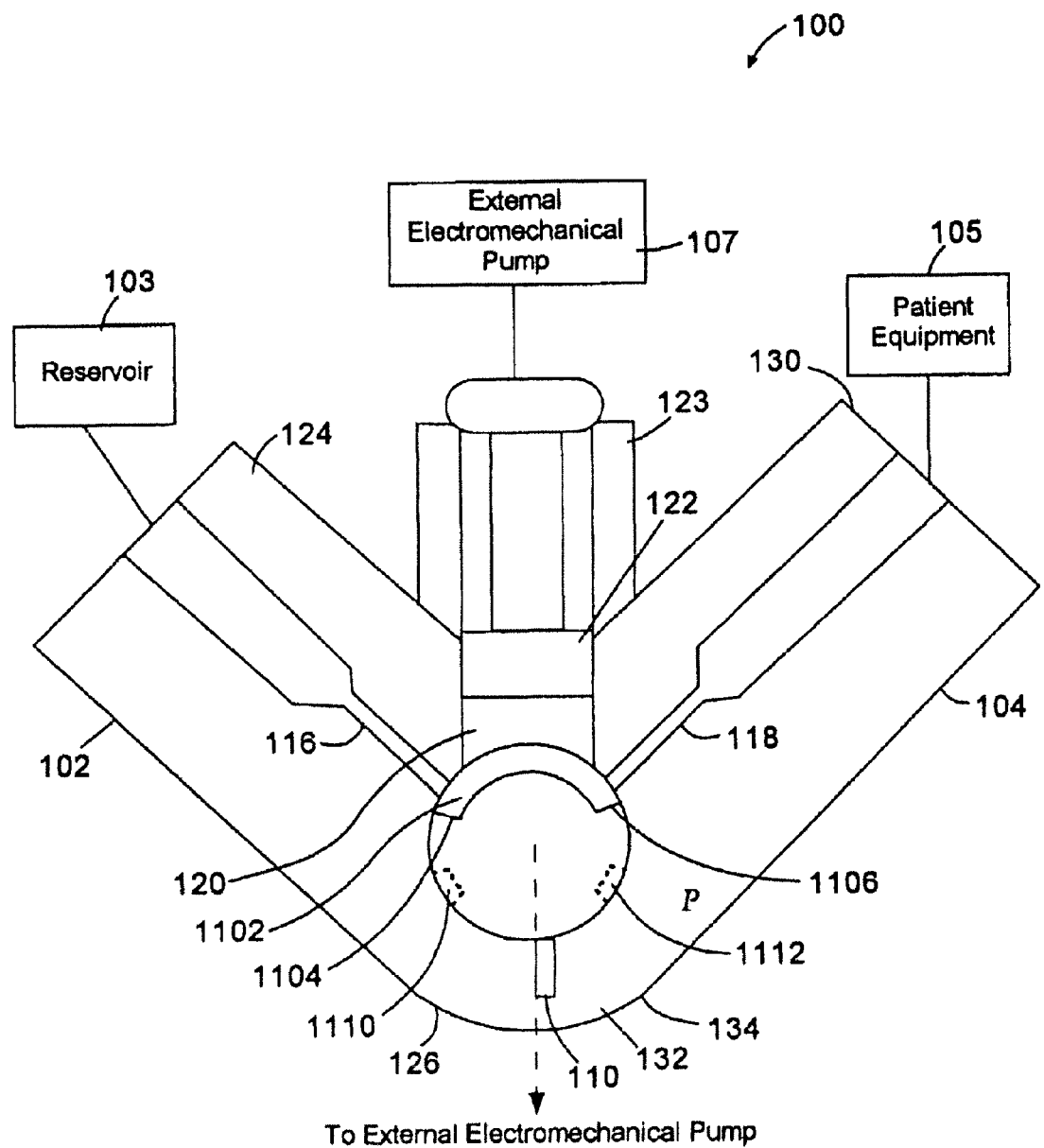
FIG. 17 is a perspective view of a fluid delivery system incorporating the rotary valve of FIG. 11, showing the valve in the priming position, in accordance with an embodiment of the present invention.

FIG. 17 is a cross-sectional view of the fluid delivery apparatus 100 with valve 1100 in the priming position. Since the pumping notches 1110 and 1112 are out of vertical alignment with fluid channels 116 and 118 (see FIG. 15), the pumping notches 1110 and 1112 are shown by dashed lines. The pumping notch 1108 on top of the priming channel notch 1102 is not shown in FIG. 17. The priming channel notch 1102 connects the fluid channel 116 with the fluid channel 118, thereby allowing priming of the fluid pump 100 and the reservoir 1132 below 1104. Note that as discussed before, the priming channel notch 1102 is selected to be at least wide enough to make fluid contact between fluid channels 116 and 118, as depicted in FIG. 17.

Figure 18:
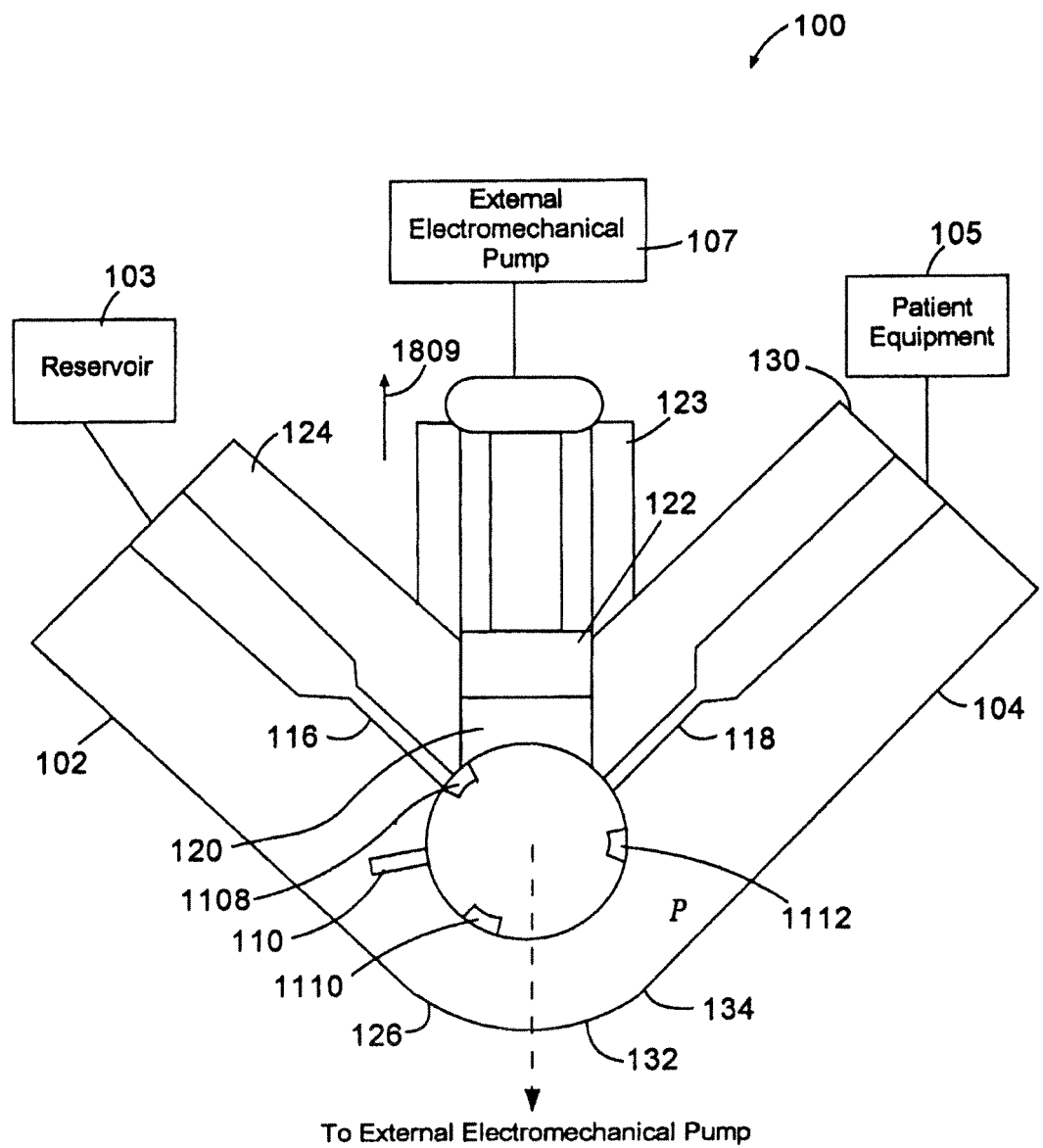
FIG. 18 is a perspective view of a fluid delivery system incorporating the rotary valve of FIG. 11, showing the valve in a first pumping position, in accordance with embodiments of the present disclosure.

FIG. 18 is a cross-sectional view of a fluid delivery apparatus 100 with valve 1100 in the I pumping position. As described above, a user can bring valve 1100 to its pumping position by pushing it into an alignment with the fluid channels 116 and 118. Because the priming channel 1102 is not vertically aligned with the fluid channels 116 and 118 (see FIG. 16), it is not shown in FIG. 18. As described before, in the I p position, the piston 122, initially in the pushed-in position, is pulled outwardly in the direction of arrow 1809, thereby expanding volume of chamber 120. The pumping notch 1108 is sufficiently wide to allow fluid from the channel 116 to pass into the chamber 120. However, the pumping notch 1108 is narrow enough that it does not allow fluid to pass into the outlet tube 104. After the piston 122 is pulled out completely in the direction of arrow 1809, the valve 1100 is rotated by an electro-mechanical system 107 into the O pumping position, and the piston 122 is pushed back inwards by the electro-mechanical system 107.

Figure 19:
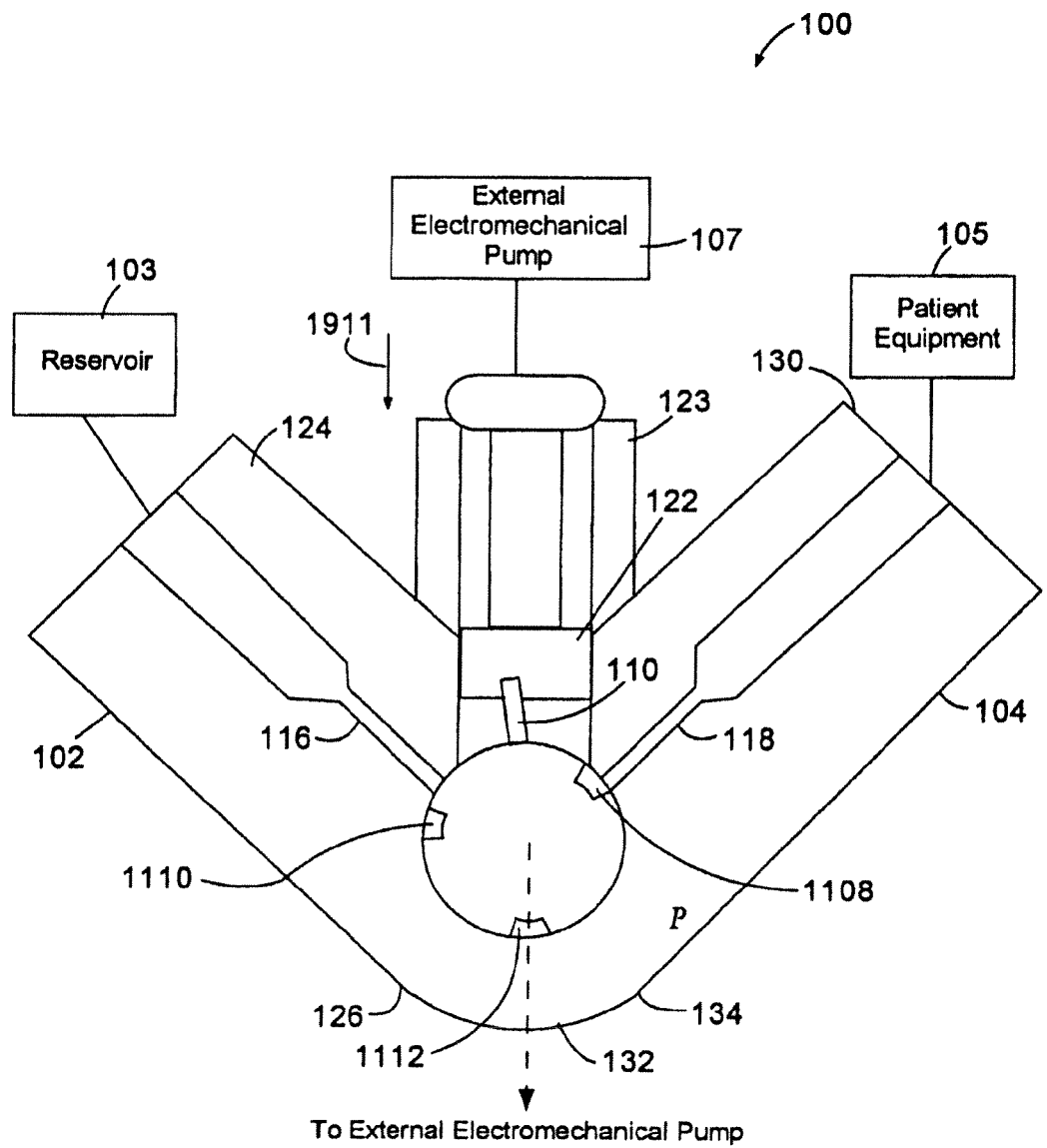
FIG. 19 is a perspective view of a fluid delivery system incorporating the rotary valve of FIG. 11, showing the valve in a second pumping position, in accordance with embodiments of the present disclosure.

FIG. 19 is a cross sectional view of the fluid pump delivery apparatus 100, with the valve 1100 in the O pumping position. In this position, the pumping channel notch 1108 establishes fluid contact between the chamber 120 and the fluid channel 118 of the outlet tube 104. As the piston 122 is pushed in, fluid from the chamber 120 is expelled into the fluid channel 118. Note that the other two pump notches 1110 and 1112 are rotated out of the fluid path completely. Upon completely pushing in the piston 122, the external electro-mechanical system then rotates the valve 1100 in the same direction (i.e., no hack-and-forth movement) so that a next notch 1110 now establishes a fluid contact between the inlet tube 102 and the chamber 120 in the I pumping position. During fluid delivery, the valve 1100 is thus rotated in the same direction, causing it to alternate between the I pumping position and the O pumping position, thereby achieving fluid delivery.

Practitioners of the art will appreciate that the above described embodiment may also be operated together with a second piston described for FIG. 4 above, including an AIL sensor. Furthermore, while the embodiment in FIGS. 11-19 shows the priming channel notch 1102 positioned adjacent to and below the pumping notches 1108, 1110 and 1112, several variations in positioning and shaping the notches are possible consistent with the principles of the present disclosure. For example, it is possible to position the priming channel notch to be above the pumping notches. It is also possible to provide a "no notch" portion between a priming channel notch and the pumping notches.

Various embodiments disclosed above provide a fluid delivery apparatus having a rotary valve. The rotary valve operates in a priming and a pumping position. A user can position the rotary valve into the priming or the pumping position by manipulating the valve. A tactile and/or visual feedback is provided to the user as an indication of position of the rotary valve. Similar feedback regarding position of the valve may also be provided to an electromechanical pump.

Figure 20:
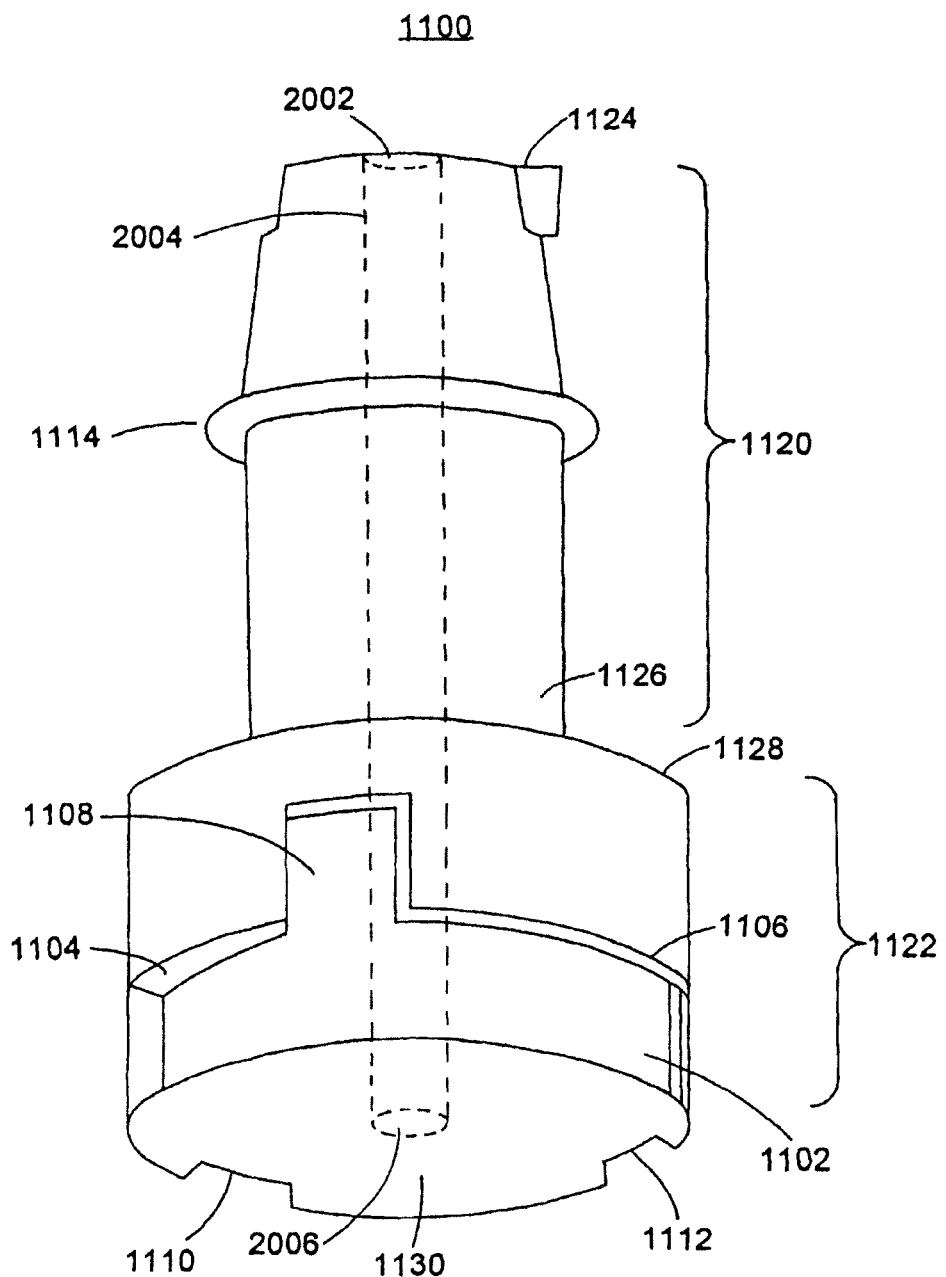
FIG. 20 is a perspective view of a valve depicting a central tubular opening, in accordance with embodiments of the present disclosure.

FIG. 20 shows another embodiment of valve 1100. In the illustrated embodiment, a hollow conduit 2004 is provided running from top to bottom of the valve 1100, with a top opening 2002 at the top of the valve and a bottom opening 2006 at the bottom of the valve 1100. The conduit 2004 may be used for accessing fluid in the delivery apparatus 100 through a secondary opening in the wall 134 of the fluid delivery apparatus 100. In certain embodiments, the opening 2002 may be fitted with a membrane (not shown in FIG. 20) that allows fluid pressure measurements. The membrane could be used by a user or an external instrument to detect pressure changes in the valve chamber 126. Pressure measurements can be performed by, for example, inserting a pin from against the membrane (not shown). In certain embodiments, a fluid access point could be provided to the opening 2002 here to allow for a SmartSite® or other fluid access point or delivery device to be attached directly to the fluid delivery apparatus 100. In certain embodiments, an air vent to vent air out of the line could be advantageously provided on the top opening 2002 because air would flow upward instead of along the fluid path.

After the user moves the rotary valve to the pumping position, an external electromechanical system rotates the rotary valve to deliver fluid from an inlet tube to an outlet tube. The fluid delivery is performed in two fluid transfer steps: a first transfer from the inlet tube to a fluid chamber with the outlet tube cut off from a fluid contact with the fluid chamber and a second transfer from the fluid chamber to the outlet tube with the inlet tube cut off from a fluid contact with the fluid chamber. The volume of fluid transferred in each fluid transfer step is controlled by movement of a piston. Because of this, the amount of fluid transferred per rotation of the valve is relatively independent of the fluid pressure in the inlet or the outlet tube. Furthermore, the fluid delivery apparatus is easily primed by a user by moving the rotary valve in the priming position and venting air out. When priming is completed, the user can rotate the valve in the pumping position. In this position, the fluid delivery apparatus is effectively turned off (fluid is not delivered) until an external electromechanical system coupled to the rotary valve beings rotating the valve along the principles disclosed in this disclosure. The rotary valve may also be used to turn off the flow by pushing the valve sufficiently down into the fluid delivery apparatus to cut off fluid connection between the inlet tube and outlet tube.

It will be appreciated by those skilled in the art that the various valve embodiments described above lend themselves to a configuration to convey fluid from the inlet tube to the outlet tube when rotated in a clockwise direction and convey fluid from the outlet tube to the inlet tube when rotated in an anticlockwise direction. Such bidirectional operation of a fluid delivery apparatus 100 can be advantageously used in a variety of clinical applications to both deliver fluid to a patient and draw fluid away from the patient or toward the original primary fluid source. For example, in certain embodiments, the bi-directional operation of a valve 108, 500 or 1100 may be utilized to back-prime a second bag of fluid into the primary source bag. In certain embodiments, the directionality of flow may be achieved by controlling the rotational direction (clockwise or anticlockwise) of the valve 100. In certain embodiments, the directionality of flow may be achieved by timing movement of piston differently with respect to valve movement. For example, in certain configurations, with the valve 108, 500 or 1100 in the pumping position(s) and the valve configured to rotate in one direction (clockwise or anticlockwise), bidirectionality of fluid delivery can be achieved as follows. Fluid can be delivered from the inlet tube 102 to the outlet tube 104 by pulling the piston 122 outwards when the fluid chamber 120 is in fluid contact with the inlet tube 102 and moving the piston 122 downwards when the fluid chamber 120 is in contact with the outlet tube 104. In the reverse direction, fluid can be delivered from the outlet tube 104 to the inlet tube 102 by pulling the piston 122 outwards when the fluid chamber 120 is in fluid contact with the outlet tube 104 and moving the piston 122 downwards when the fluid chamber 120 is in contact with the inlet tube 102.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A method of delivering fluid from an inlet tube connected to a fluid reservoir to an outlet tube in a pumping cycle; the method comprising:

positioning, during an inflow phase of the pumping cycle, a valve to a first pumping position to establish a fluid contact between the inlet tube and a first aspiration cavity without having a fluid connection between the first aspiration cavity and the outlet tube, wherein positioning the valve to the first pumping position comprises rotating the valve to partially align a wedge shaped opening in the valve with the inlet tube and with the first aspiration cavity and fluidically isolating a priming tubule from the outlet tube, the priming tubule fluidically coupled to the wedge shaped opening;

moving, during the inflow phase, a first piston coupled with the first aspiration cavity to increase the volume of the first aspiration cavity;

positioning, during an outflow phase of the pumping cycle, the valve to a second pumping position to establish a fluid contact between the first aspiration cavity and the outlet tube without having a fluid connection between the inlet tube and the first aspiration cavity, wherein:

positioning the valve to the second pumping position comprises rotating the valve to partially align the wedge shaped opening in the valve with the outlet tube and with the first aspiration cavity;

moving, during the outflow phase, the first piston to decrease the volume of the first aspiration cavity;

operating a second piston connected to the outlet tube to divert a portion of the fluid from the first aspiration cavity into a second aspiration cavity in the outlet tube during the outflow phase thereby reducing a fluid delivery pulsation; and delivering, from the second aspiration cavity to the outlet tube, the diverted portion of fluid during the inflow phase.

2. The method of claim 1, wherein the second piston is different from the first piston.

3. The method of claim 1, wherein the volume of the second aspiration cavity is less than the volume of the first aspiration cavity.

4. The method of claim 3, wherein the volume of the second aspiration cavity is one-half of the volume of the first aspiration cavity.

5. The method of claim 1, wherein rotating the wedge shaped opening in the valve comprises synchronizing a valve rotation with the moving of the first piston and the moving of the second piston.

6. The method of claim 1, wherein positioning the valve in the second position comprises griping a handle and rotating the valve from the first position to the second position.

7. The method of claim 6, further comprising fluidly decoupling the inlet tube from a first channel notch and fluidly decoupling the outlet tube from a second channel notch, when the valve is in a priming position.

8. The method of claim 1, further comprising coupling the inlet tube and the outlet tube with the priming tubule when the valve is in a priming position.

9. The method of claim 1, further comprising adjusting a rate of fluid flow by turning the valve to either end of a priming channel notch during a priming operation.

10. The method of claim 1, wherein positioning the valve to a first pumping position comprises coupling the inlet tube to the first aspiration cavity through a pumping notch.

11. The method of claim 1, further comprising:
rotating the valve to a first priming position;
pulling the valve in a direction away from a fluid channel in the inlet tube and a fluid channel in the outlet tube;
stopping the valve movement when a base portion touches a distal end of the inlet tube and the outlet tube;
aligning a priming channel notch with the inlet tube and the outlet tube; and
venting air out of the valve through the priming channel notch.

12. The method of claim 1, further comprising placing the valve in a priming position wherein the inlet tube, the outlet tube, and the first aspiration cavity are fluidly coupled through a priming channel notch.

13. The method of claim 1, further comprising rotating the valve in a first direction to convey fluid from the inlet tube to the outlet tube; and rotating the valve in a second direction to convey fluid from the outlet tube to the inlet tube.

14. The method of claim 13, further comprising rotating the valve in the first direction to deliver fluid to a patient, and rotating the valve in the second direction to draw fluid away from the patient.

15. The method of claim 1, further comprising timing the movement of the first pumping piston and the second pumping piston with a rotating of the valve to obtain a bidirectional fluid flow.

16. The method of claim 1, further comprising back-priming a second bag of fluid into a primary source bag of fluid using a bidirectional fluid flow between the inlet tube and the outlet tube.

17. The method of claim 1, wherein positioning the valve in the first pumping position and the second pumping position comprises fluidly decoupling the inlet tube and the outlet tube.

18. The method of claim 1, further comprising measuring a fluid pressure using a membrane fitted on a top opening of a hollow conduit running from a top side to a bottom side of the valve.

19. The method of claim 1, further comprising venting air through a top opening of a hollow conduit running from a top side to a bottom side of the valve.

20. The method of claim 1, further comprising providing a feedback to a user as an indication of a position of the valve, the feedback comprising at least one of a tactile and a visual feedback.

* * * * *